United States Patent [19]

Rondelet et al.

[11] Patent Number: 5,295,967
[45] Date of Patent: Mar. 22, 1994

[54] SYRINGE PUMP HAVING CONTINUOUS PRESSURE MONITORING AND DISPLAY

[75] Inventors: Jean-Claude Rondelet, Etienne de Crossey; Jean-Michael Dupouy, La Tronche, both of France

[73] Assignee: Becton, Dickinson and Company, Franklin Lakes, N.J.

[21] Appl. No.: 949,610

[22] Filed: Sep. 23, 1992

[51] Int. Cl.⁵ .............................................. A61M 5/20
[52] U.S. Cl. ............................ 604/154; 128/DIG. 12; 604/67
[58] Field of Search .................. 604/154, 155, 67, 65; 128/DIG. 12, DIG. 13

[56] References Cited

U.S. PATENT DOCUMENTS

| | | | |
|---|---|---|---|
| 2,742,901 | 4/1956 | Krauthamer | 604/154 |
| 4,624,658 | 11/1986 | Mardorff et al. | 604/154 |
| 4,741,732 | 5/1988 | Crankshaw | 604/155 |
| 4,767,406 | 8/1988 | Wadham et al. | 604/155 |
| 4,902,277 | 2/1990 | Mathies et al. | 604/154 |
| 4,950,246 | 8/1990 | Muller | 604/154 |
| 4,952,205 | 8/1990 | Maurer et al. | 604/154 |
| 5,034,004 | 7/1991 | Crankshaw | 604/154 |
| 5,087,245 | 2/1992 | Doan | 604/67 |
| 5,140,862 | 8/1992 | Pappalardo | 604/154 |

OTHER PUBLICATIONS

Lymphography Injector, c. 1972 Cat. No. 404-100, Copy in 604/155, Gp. 330.

Primary Examiner—Paul J. Hirsch
Attorney, Agent, or Firm—Michael G. Schwarz

[57] ABSTRACT

A syringe pump is disclosed having a transducer for detecting the force on the syringe pusher. The detected force is translated into a pressure which is continuously displayed so that the user can anticipate the occurrence of an occlusion. The syringe pump also has a device for pre-selecting a range of acceptable pressures.

7 Claims, 11 Drawing Sheets

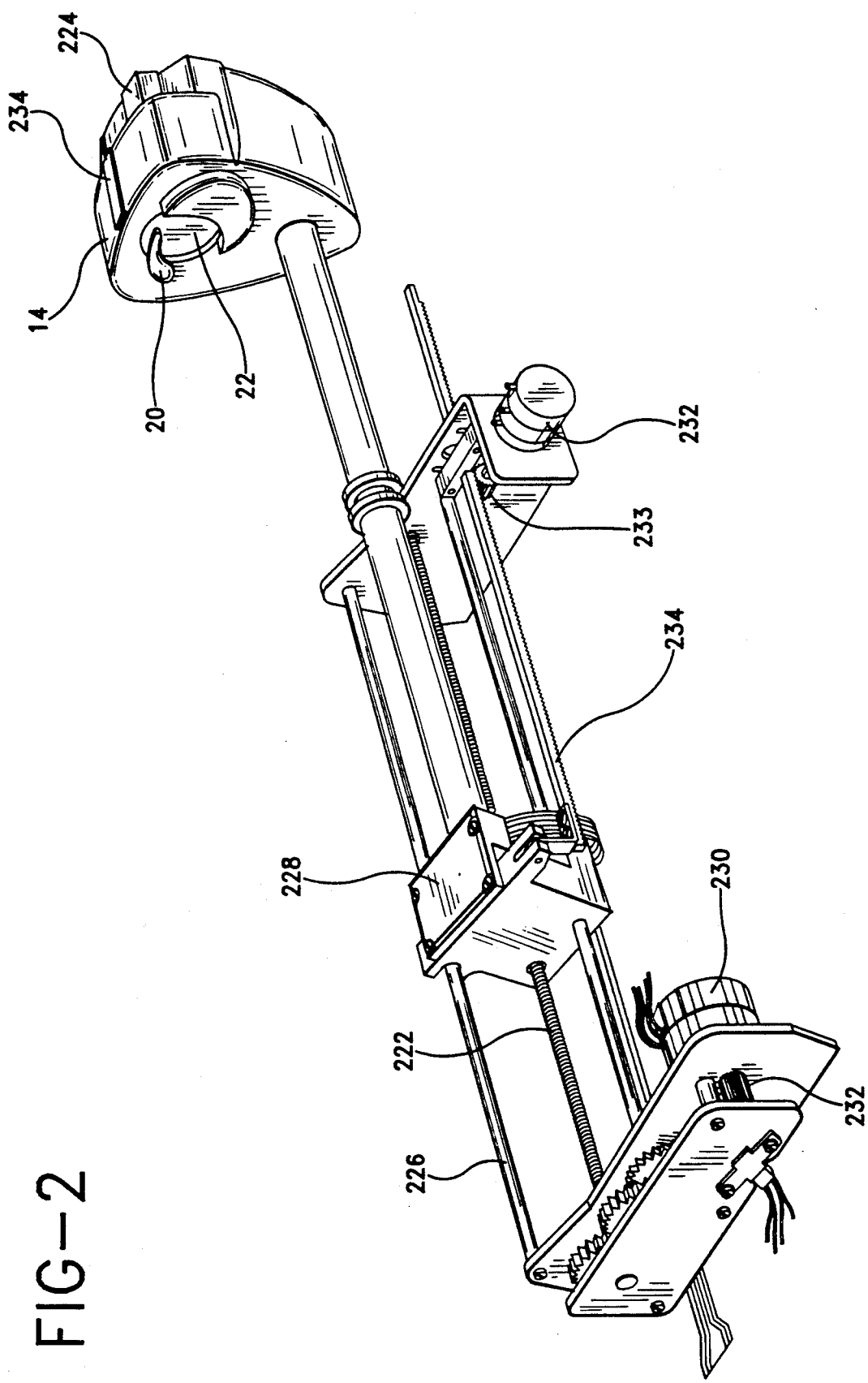

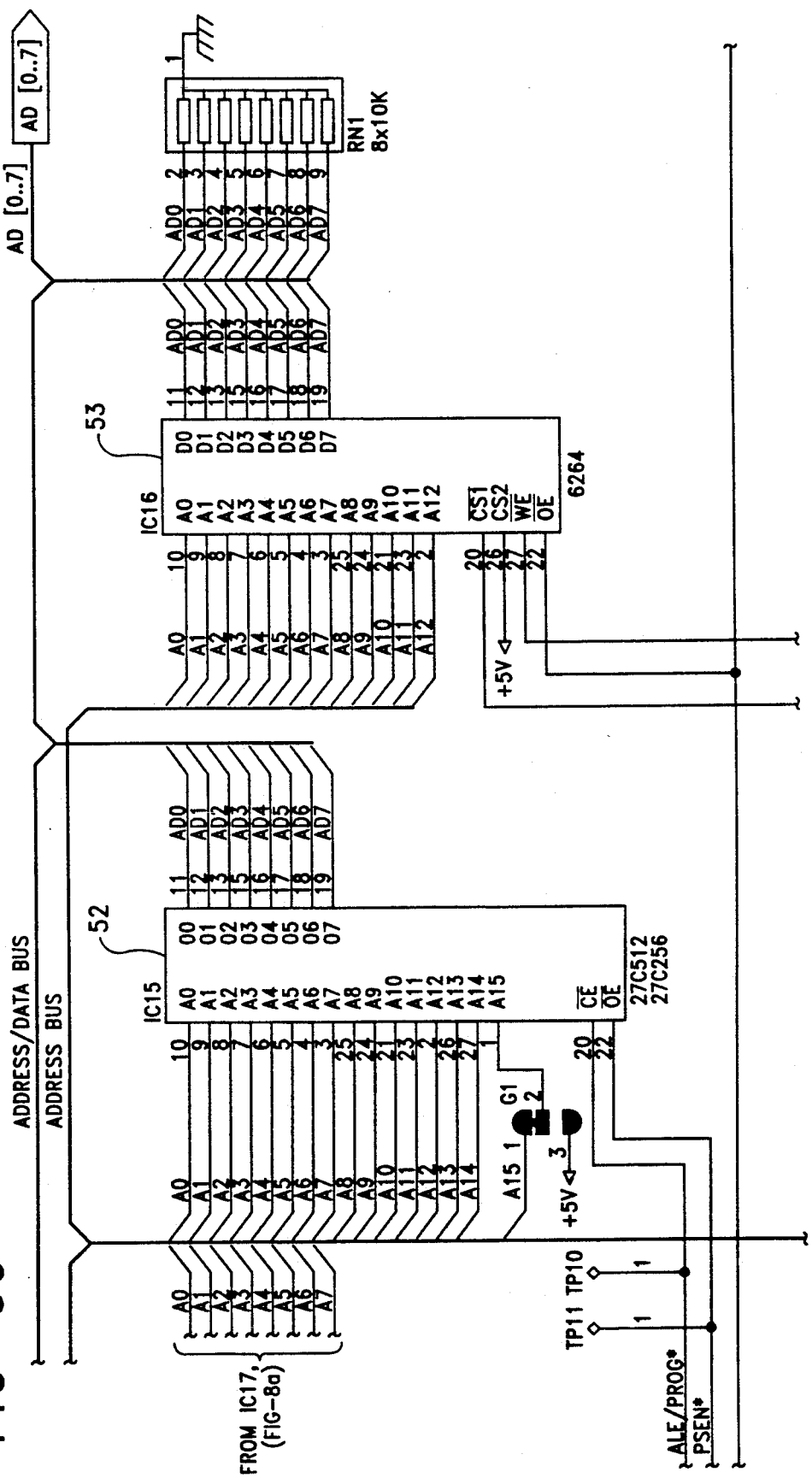

SYRINGE PUMP HAVING CONTINUOUS PRESSURE MONITORING AND DISPLAY

BACKGROUND

FIELD OF THE INVENTION

The invention relates generally to the field of syringe pumps. In particular, the invention relates to a syringe pump having a continuous pressure monitoring and display device.

BACKGROUND

A syringe pump is a device for pumping fluid from a syringe into a patient. The syringe is placed in the pump and connected to the patient via an infusion line. During the course of infusing medication into a patient, it is possible for an occlusion to arise in the infusion line. Such a condition, if undetected may cause injury to the patient.

An occlusion in the infusion line will cause the pressure in the syringe to increase. This in turn will cause the force between the pusher of the syringe pump and the syringe plunger to increase. Syringe pumps exist in the prior art in which the force between the pusher of the syringe pump and the syringe plunger or the pressure in the syringe are monitored. In prior art pumps, when the force between the pusher and the plunger or the pressure in the syringe increased above a predetermined threshold, an alarm was generated. This alarm was essentially a binary alarm. That is to say, it was either "on" or "off." Therefore, the user of the syringe pump would not know whether the pressure in the syringe was building up to an unacceptable level. The user would only know when the alarm limit was reached. Thus, remedial action could only be taken once the user was aware of the occlusion. The binary nature of the alarm therefore prevented preemptive action from being taken to remove the occlusion prior to the alarm limit being reached.

SUMMARY OF THE INVENTION

The invention is a syringe pump in which the pushing force on the syringe plunger is continuously measured and displayed so that the user can monitor the development of occlusions in the infusion line. The invention is made up of a syringe pump having a housing on which a syringe is mounted. The syringe plunger is pushed by means of a motor driven pusher. A transducer is provided to measure the force on the pusher. The force on the pusher is translated into a pressure and the pressure is displayed on a pressure display.

The syringe pump may also include means for selecting ranges of occlusion pressures so that the user may monitor the pressure inside the syringe and insure that it remains within the pre-selected range. The invention also displays the actual pressure in the syringe.

BRIEF DESCRIPTION OF THE DRAWINGS

FIG. 2 is a perspective view of the drive mechanism of the syringe pump;

FIG. 6a-f are schematic diagrams of the electronics of the invention; and

DETAILED DESCRIPTION OF THE DRAWINGS

Figure 1:
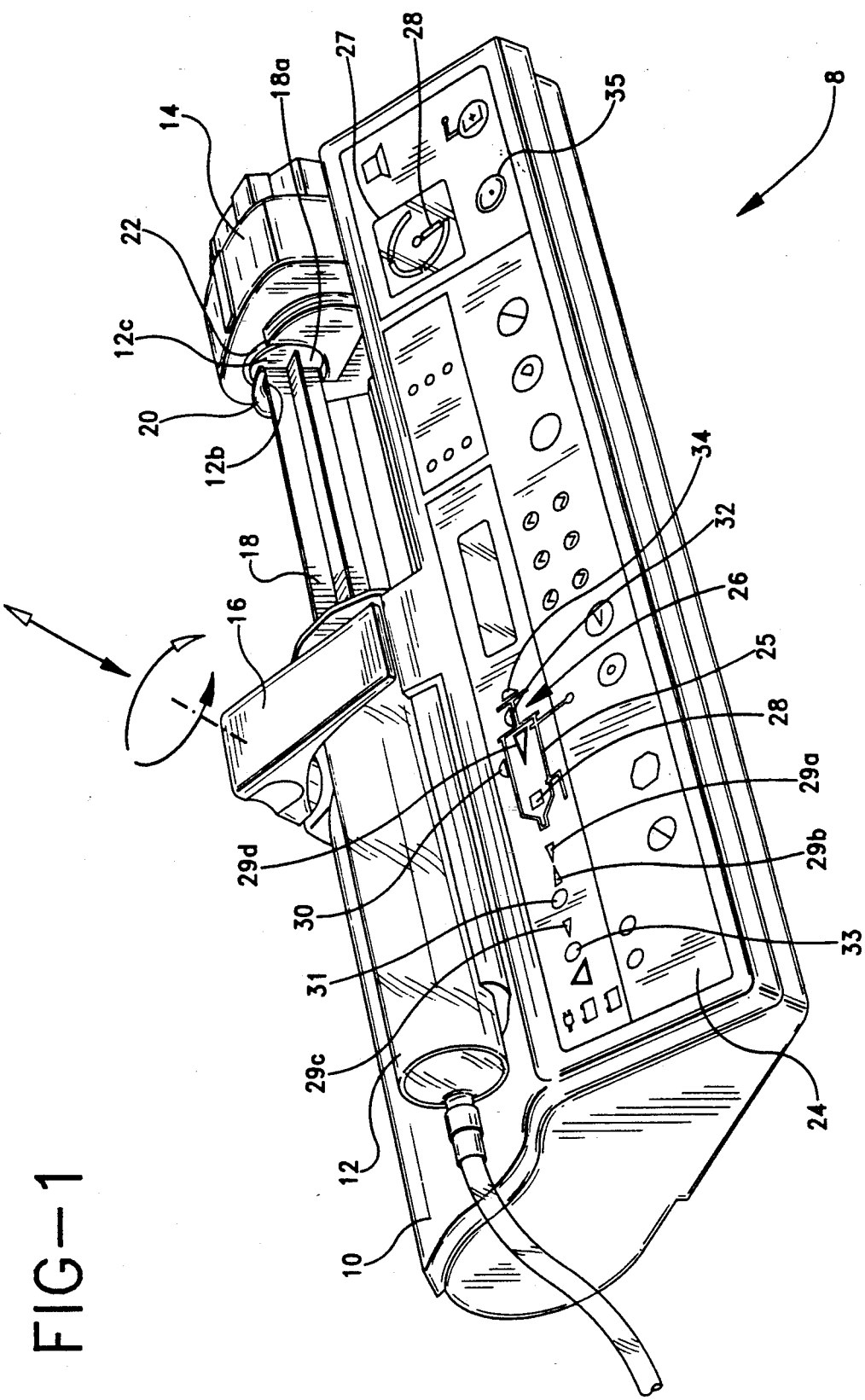
FIG. 1 is a perspective view of a syringe pump embodying the invention.

A syringe pump 8 embodying the invention is shown in FIG. 1. Housing 10 supports syringe 12, pusher 14 and syringe clamp 16. Syringe clamp 16 holds syringe 12 in place on housing 10. Plunger 18 of syringe 12 is pushed by pusher 14 which is driven by an electric motor via a lead screw (see FIG. 2).

Pusher 14 is provided with antisiphon catch 20 which engages flange 18a of plunger 18, thus preventing plunger 18 from moving independently of pusher 14. Pusher 14 is also provided with pressure plate 22 for pushing directly against flange 18a thereby pumping fluid from syringe 12.

FIG. 2 shows the chassis and mechanical components of pump 8. Chassis 226 carries motor 230 and lead screw 222. Motor 230 drives lead screw 222 via gear assembly 232. Pusher 14 is driven by the interaction of pusher block 228 with lead screw 222. Pusher block contains half nuts 322, 324 which interact with lead screw 222 (see FIG. 3).

Figure 5:
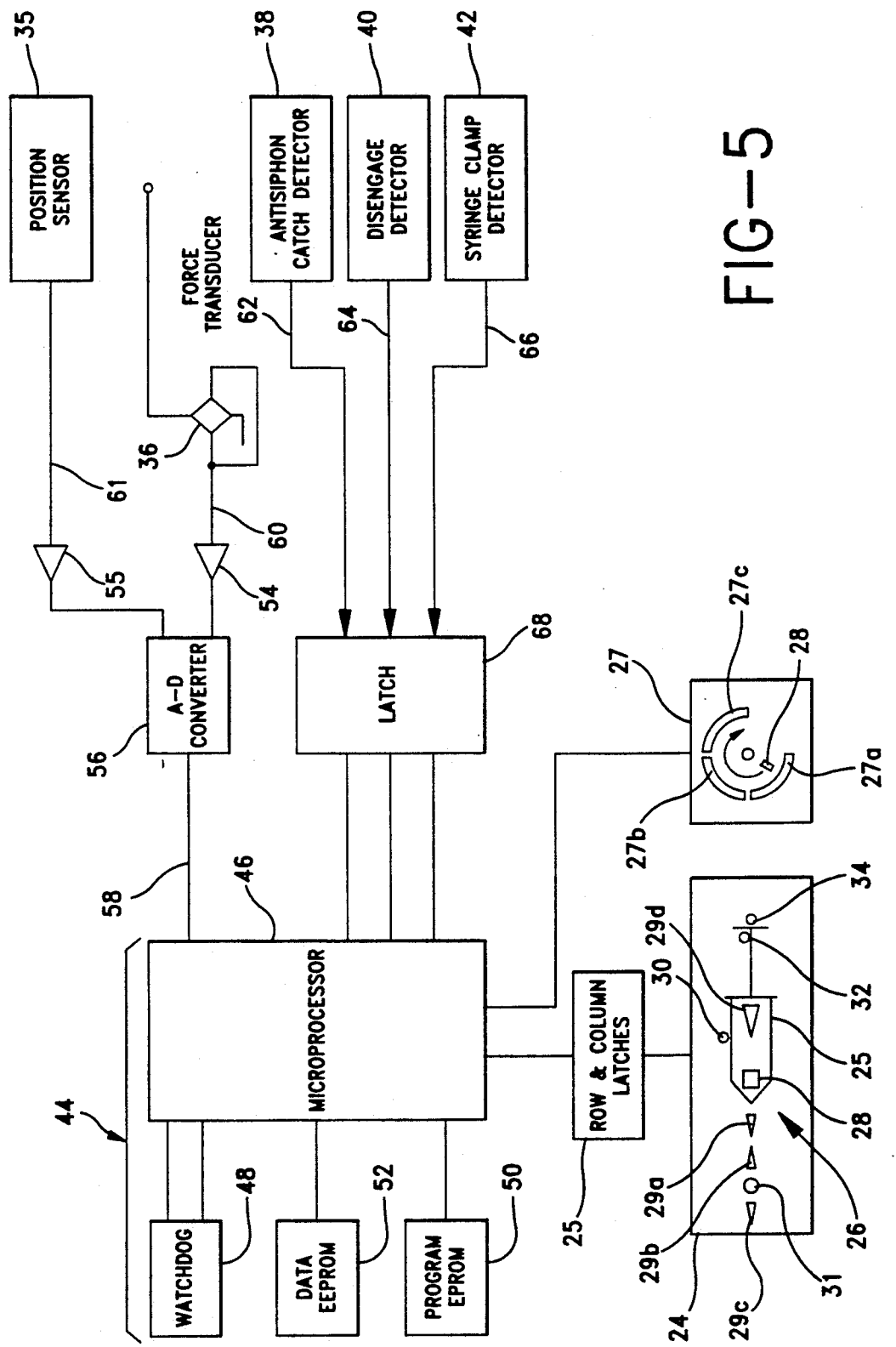
FIG. 5 is a block diagram of the main components of the invention.

FIG. 5 is a block diagram showing the main electronic components of the invention. Transducers are provided to detect various parameters of the syringe pump which are displayed on panel 24. The transducers are: force transducer 36, antisiphon catch detector 38, disengage detector 40 and syringe clamp detector 42. The outputs of these transducers 60, 62, 64 and 66 respectively are fed into central processing unit 44 via various signal processing modules. Schematic diagrams of the various electronics modules are shown in FIGS. 8a. The values and types of the components are indicated on the schematic diagrams.

Figure 6A:
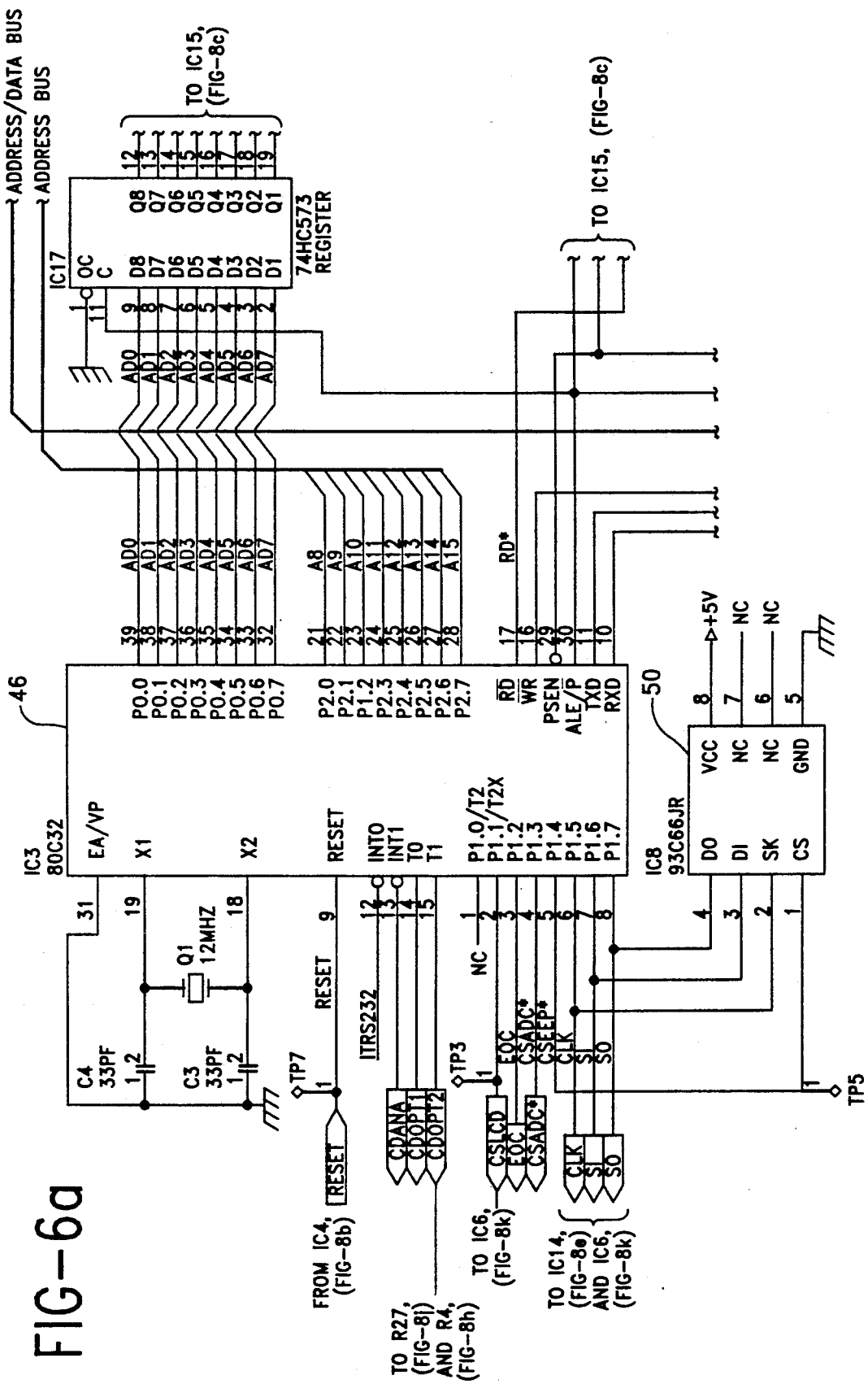
Figure 6B:
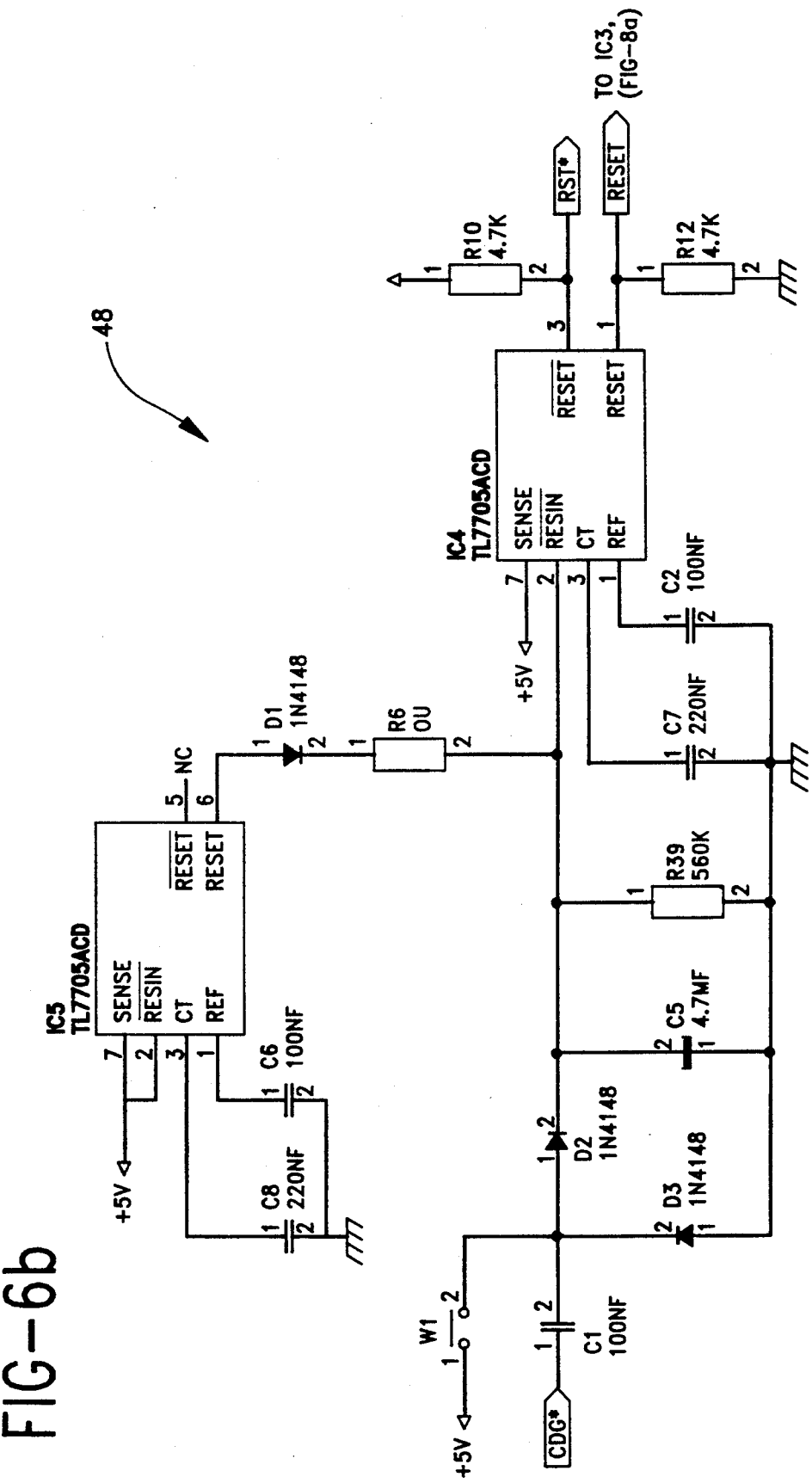

Central processing unit 44 comprises microprocessor 46 (FIG. 6a) with random access memory 53 (FIG. 8a), watchdog 48 (FIG. 6b), EPROM 50 (FIG. 6a) and EEPROM 52 (FIG. 6c). Watchdog 48 monitors microprocessor 46 to ensure its proper operation. EEPROM 52 contains data concerning the parameters of the syringes used in the pump. EPROM 50 contains a software program which controls the operation of the syringe pump.

Figure 6D:
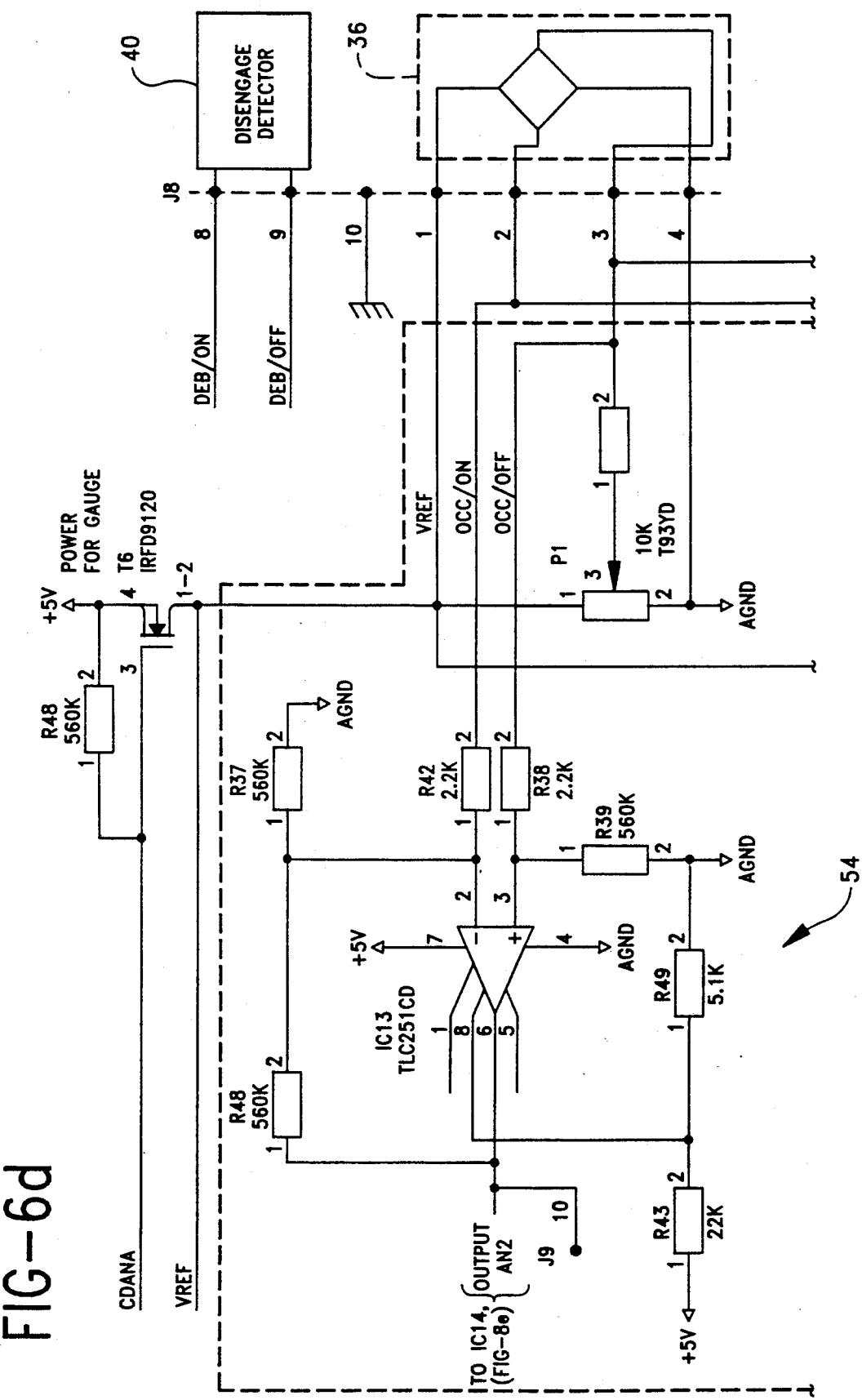
Figure 6E:
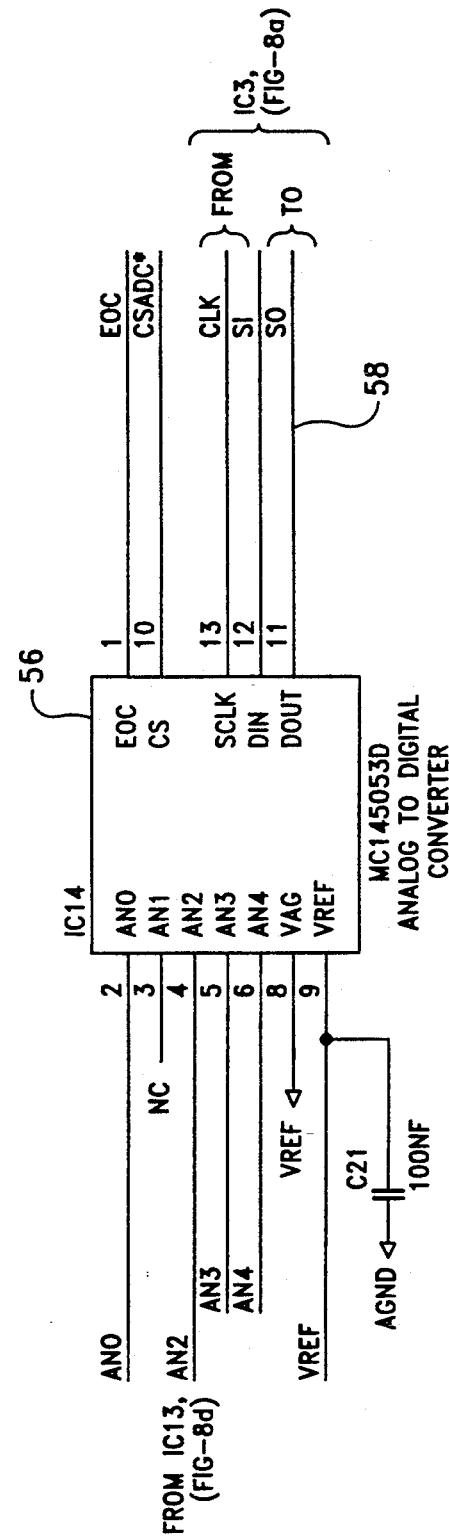

The output of force transducer 36 is conditioned by signal conditioning circuit 54 (FIG. 6d), which converts the output of force transducer 36 into a form suitable for input into analog to digital converter 56 (FIG. 6e). Analog to digital converter 56 digitizes the analog output and produces serial output 58 which is in turn fed into input port 60 of microprocessor 46.

Figure 4:
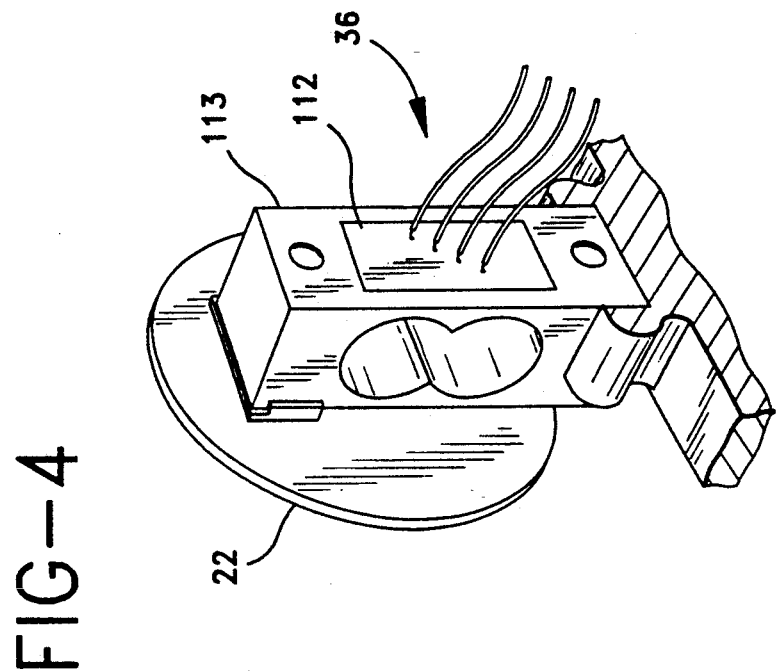
FIG. 4 is a perspective view of the pusher disc and force transducer.

FIGS. 4 shows force transducer 36 in greater detail. Force transducer 36 is made up of four strain gauges in a wheatstone bridge configuration. The bridge has an impedance of 350 ohms or 1 Kohm with a tolerance of +/−15%. The range of force measurements is 0 to 150N. The bridge sensitivity is 1.7 mV/V to 2.4 mv/V under a load of 150N at 20 degrees centigrade. The bridge is powered intermittently under the control of microprocessor 46 (line CDANA in FIGS. 6a and 6d) in order to conserve energy.

Figure 3:
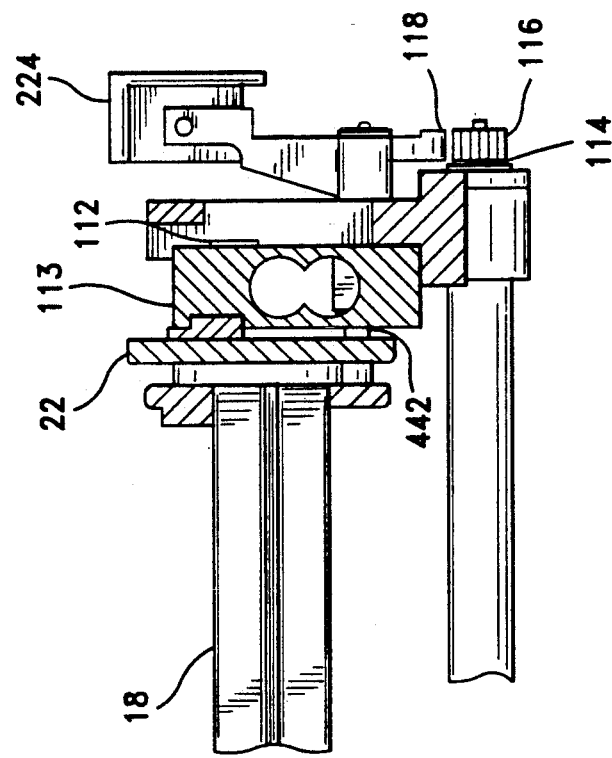
FIG. 3 is a cross sectional view of the pusher mechanism of the invention.

As seen in FIGS. 3 and 4, strain gauges 112 are glued onto beam 114. When force is applied to pressure plate 22, beam 114 flexes, causing strain gauges 112 to distort and produce output 60.

Output 60 of force transducer 36 is fed into conditioning module 54 (FIG. 6d) and thereafter into analog to digital converter 56 which converts the conditioned output of force detector 36 into serial output 58. Serial output 58 is then fed into input 60 of microprocessor 46.

Resident in EPROM 50 is a software program for microprocessor 46 which calculates the pressure inside syringe 12 continuously as the force on the plunger 18 is measured by force transducer 36. Certain parameters which are used by the program to calculate the pressure in the syringe and stored in EPROM 52. Since syringe pump 8 is programmable to accommodate various types of syringe, a set of parameters for each type of syringe, is stored in EPROM 52.

The parameters stored in EEPROM 52 include:

Ff=average frictional force between the syringe plunger and the syringe barrel at null (atmospheric) pressure.

PC=the pressure in the syringe when a calibration force is applied to the plunger. The calibration force is typically 5 kgF and leads to a value of Pc of around 0.7 bar, a usual pressure threshold.

Fc=the force with which the plunger is loaded to obtain a pressure of Pc in the syringe.

The program in EPROM 50 is used by microprocessor 46 to calculate the pressure in the syringe. Microprocessor 46 then compares the calculated pressure with a pressure value or values stored in EEPROM 52 for that syringe. If the calculated pressure exceeds the stored pressure, an occlusion alarm is generated by microprocessor 46.

The algorithm for calculating the pressure in the syringe is:

$$P = \frac{(F - Ff)}{Fc - Ff} \cdot Pc$$

where F is the force measured by force transducer 36 and Fc, Ff and Pc are the parameters defined above.

The main advantages of this formula over the traditional formula described in the BACKGROUND section above are (1) it is not highly dependent on the frictional force in the syringe which is known to vary with pressure and (2) that the cross-sectional area of the syringe need not be determined. Rather, the pressure in the syringe is calculated using parameters which are easy to determine empirically.

Thus it can be seen that the error in the pressure measurement using the present invention is substantially reduced in comparison to that of the prior art.

Figure 6F:
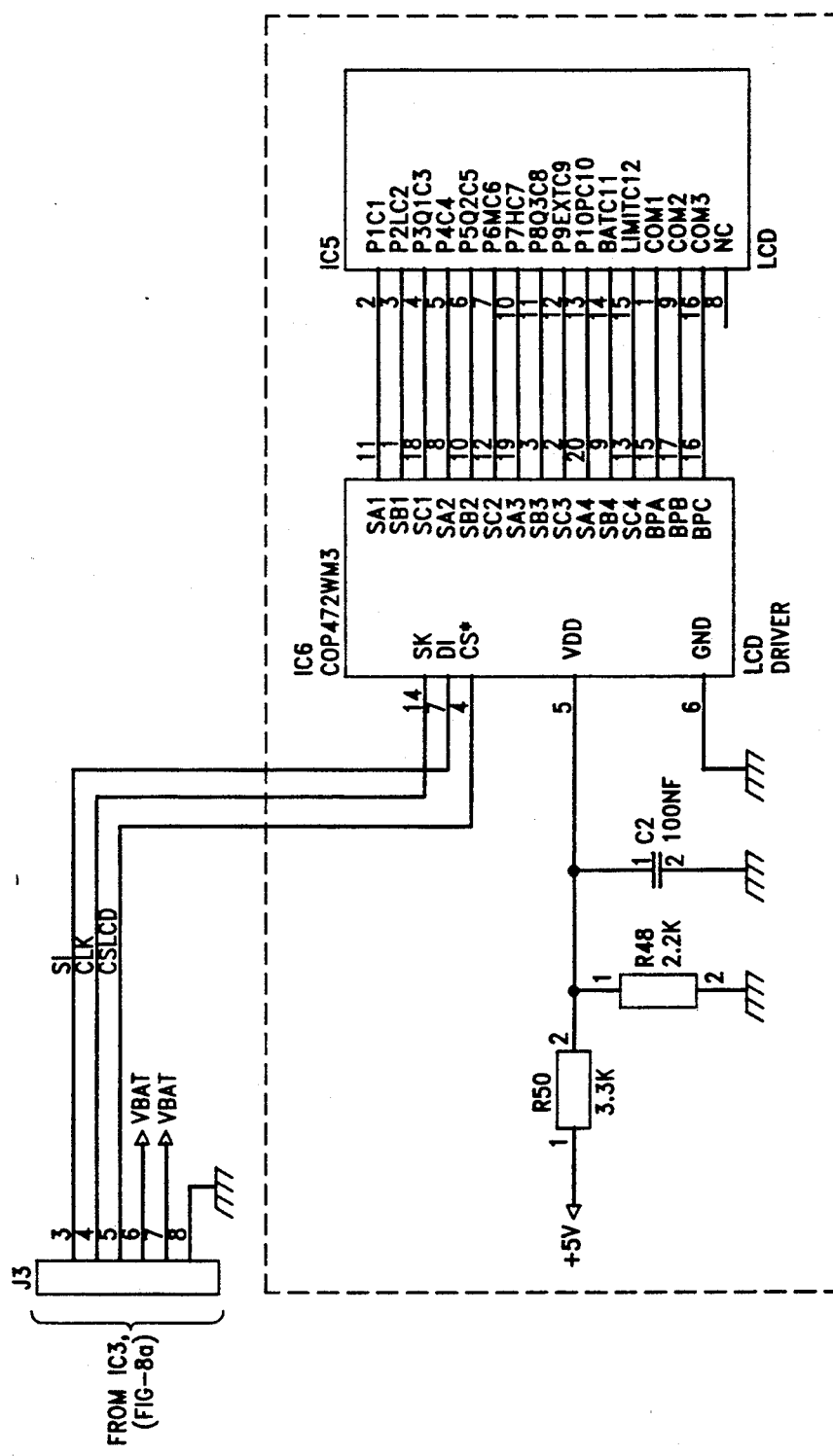
Figure 7:
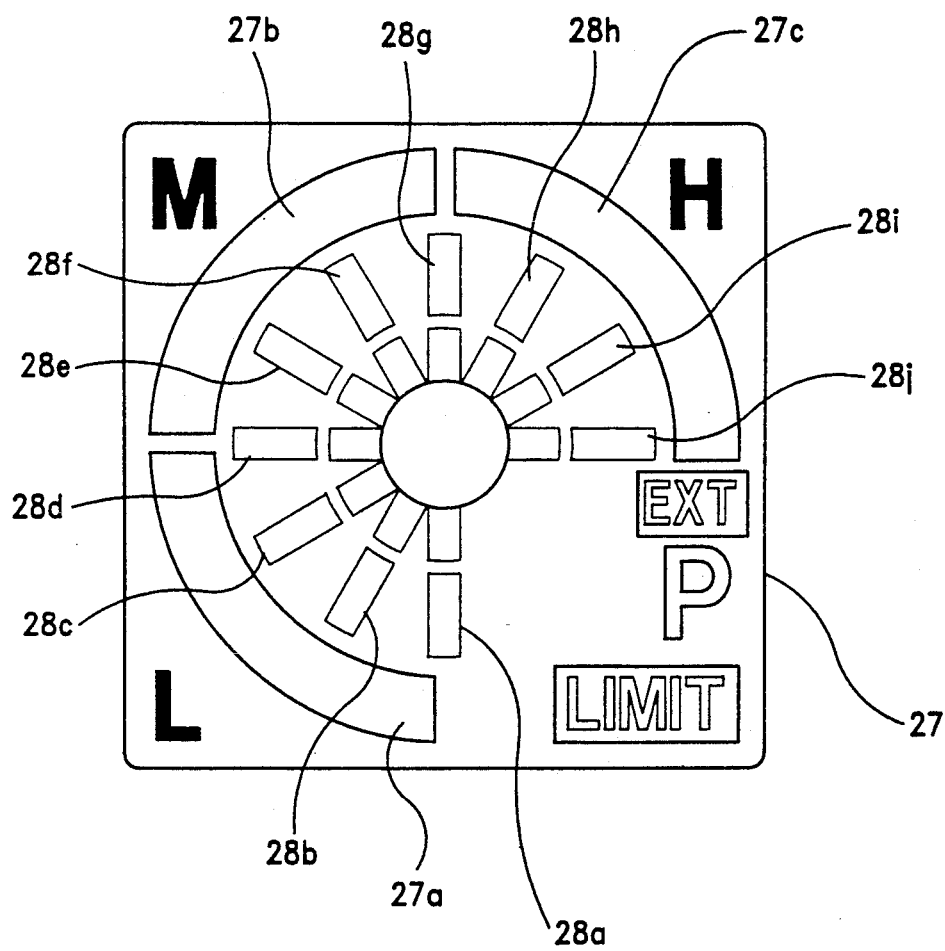
FIG. 7 is a diagram showing the segments of the pressure display.

Pressure display 27 is supplied with data from microprocessor 46. Microprocessor 46 calculates the pressure in syringe 12 and outputs the calculated pressure to display 27 via a serial data bus 29 (SI in FIGS. 6a and 6f). Display 27 (See FIG. 7) is a liquid crystal display made up of three segments 27a, 27b and 27c. Segments 27a, 27b and 27c correspond to low, medium and high pressure ranges which may be pre-selected by the user using switch 35 on panel 24 (FIG. 1). Switch 35 is linked to microprocessor 46 which communicates the selection of segments 27a, 27b or 27c via serial bus 29. Display 27 also includes pointer 28 which indicates the measured pressure to the user.

Pointer 28 is made up of segments 27a-j each of which corresponds to a measured pressure. LCD driver (IC6 in FIG. 8f) actuates segments 27a, 27b or 27c depending on the pressure range selected by the user. The LCD driver also actuates the segment in 27a-j which corresponds to the pressure data provided by microprocessor 46. Thus, the user is provided with a digital display providing information as to (1) whether the pressure in the syringe is approaching a pre-set occlusion pressure and (2) what the actual pressure in the syringe is. The number of segments results in an analog form despite the fact that it is implemented by means of a digital segmented display. This allows the user to take remedial action well before an occlusion becomes a problem. It also permits more accurate use of the syringe pump.

What is claimed is:

1. A syringe pump for pumping fluid from a syringe, the pump comprising:
   means for detecting the pressure in the syringe substantially continuously; and
   means for displaying the pressure in the syringe substantially continuously such that the pressure in the syringe can be monitored during pumping.

2. The syringe pump of claim 1 wherein the means for detecting the pressure comprises:
   means for measuring the force on the plunger of the syringe; and
   means for converting the measured force to a pressure.

3. The syringe pump of claim 1 further comprising:
   means for selecting an acceptable pressure range in the syringe; and
   means for indicating the selected acceptable pressure range.

4. The syringe pump of claim 3 wherein the means for displaying comprise a digital segmented display.

5. The syringe pump of claim 4 wherein the digital segmented display comprises means for displaying the pressure in analog form.

6. The syringe pump of claim 3 wherein the means for displaying comprise a pointer for indicating the pressure in the syringe.

7. The syringe pump of claim 3 wherein the means for indicating the selected acceptable pressure range comprise three regions, a first region for low pressures, a second region for medium pressures and a third region for high pressures.

* * * * *